(12) United States Patent
Parsa et al.

(10) Patent No.: US 10,660,866 B2
(45) Date of Patent: May 26, 2020

(54) RETINOL OIL COMPOSITION

(71) Applicant: Johnson & Johnson Consumer Inc., Skillman, NJ (US)

(72) Inventors: Ramine Parsa, Lawrenceville, NJ (US); Anne-Sophie Brillouet, Pennington, NJ (US); Michael Chang, Summit, NJ (US); Star Marie Walsh, Upper Black Eddy, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 16/365,932

(22) Filed: Mar. 27, 2019

(65) Prior Publication Data

US 2020/0078317 A1    Mar. 12, 2020

Related U.S. Application Data

(60) Provisional application No. 62/728,941, filed on Sep. 10, 2018.

(51) Int. Cl.
| | | |
|---|---|---|
| *A61K 31/07* | (2006.01) |
| *A61Q 19/08* | (2006.01) |
| *A61Q 19/06* | (2006.01) |
| *A61Q 19/00* | (2006.01) |
| *A61P 17/10* | (2006.01) |
| *A61P 17/00* | (2006.01) |
| *A61K 47/06* | (2006.01) |
| *A61P 17/16* | (2006.01) |
| *A61K 8/34* | (2006.01) |
| *A61K 8/36* | (2006.01) |
| *A61K 8/31* | (2006.01) |
| *A61K 47/10* | (2017.01) |
| *A61K 47/12* | (2006.01) |
| *A61K 8/67* | (2006.01) |

(52) U.S. Cl.
CPC ............... *A61K 31/07* (2013.01); *A61K 8/31* (2013.01); *A61K 8/342* (2013.01); *A61K 8/361* (2013.01); *A61K 8/671* (2013.01); *A61K 47/06* (2013.01); *A61K 47/10* (2013.01); *A61K 47/12* (2013.01); *A61P 17/00* (2018.01); *A61P 17/10* (2018.01); *A61P 17/16* (2018.01); *A61Q 19/00* (2013.01); *A61Q 19/06* (2013.01); *A61Q 19/08* (2013.01)

(58) Field of Classification Search
None
See application file for complete search history.

(56) References Cited

U.S. PATENT DOCUMENTS

| | | | | |
|---|---|---|---|---|
| 6,015,568 A | * | 1/2000 | Segot | A61K 8/671 424/401 |
| 9,387,160 B2 | | 7/2016 | Oddos et al. | |
| 2015/0265510 A1 | * | 9/2015 | Johncock | C09C 1/3661 424/401 |

* cited by examiner

*Primary Examiner* — Nannette Holloman
(74) *Attorney, Agent, or Firm* — Sharon E. Hayner

(57) ABSTRACT

The present invention provides a composition comprising (i) about 0.05 to about 0.5% by weight retinol; (ii) a polar emollient selected from the group consisting of propylene glycol stearyl ether dicaprylyl carbonate, propylene glycol isostearate and combinations thereof; and (iii) isohexadecane, wherein the weight ratio of polar emollient to isohexadecane is 1:1 or lower and the composition is anhydrous.

6 Claims, No Drawings

RETINOL OIL COMPOSITION

CROSS-REFERENCE TO RELATED APPLICATIONS

This application claims the benefit of U.S. provisional application 62/728,941 filed on Sep. 10, 2018, the complete disclosure of which is hereby incorporated herein by reference for all purposes.

FIELD OF THE INVENTION

The present invention relates to a composition comprising (i) about 0.05 to about 0.5% by weight retinol; (ii) a polar emollient selected from the group consisting of propylene glycol stearyl ether, dicaprylyl carbonate, propylene glycol isostearate and combinations thereof; and (iii) isohexadecane, wherein the weight ratio of polar emollient to isohexadecane is 1:1 or lower and the composition is anhydrous.

BACKGROUND OF THE INVENTION

Retinol is a well-known active ingredient in cosmetics. Retinol has proven to be a highly efficacious and cost-effective ingredient for treating skin over the last 20 years, but improvements in its activity and delivery, along with new product forms are always desirable.

U.S. Pat. No. 9,387,160 relates to oil-in-water compositions containing retinol that exhibit a controlled rate of release of retinol to the skin, thereby providing both increased retinol activity and decreased irritation. The composition comprises a non-polar emollient and a polar emollient. In one embodiment the composition comprises about 0.05 to about 0.5% by weight of retinol, propylene glycol stearyl ether (PPG stearyl ether), and isohexadecane, wherein the weight ratio of propylene glycol stearyl ether to isohexadecane is from about 75:25 to about 50:50.

Similarly, NEUTROGENA® Rapid Wrinkle Repair®, commercially available from Johnson & Johnson Consumer Inc., is an oil-in-water composition containing retinol, propylene glycol stearyl ether, and isohexadecane. It is used to fade the look of wrinkles in skin, smooth fine lines, improve skin texture, and brighten skin tone.

Applicants have now discovered that anhydrous or oil compositions containing retinol may also be formulated with a polar emollient and isohexadecane. However, surprisingly, in anhydrous compositions, the weight ratio of polar emollient to isohexadecane required to obtain good retinol activity but low irritation is the reverse of that needed in oil-in-water emulsions, such as those described in the '160 patent. Specifically, in anhydrous compositions, the weight ratio of polar emollient to isohexadecane required to obtain high retinol activity-to-low irritation levels is 1:1 or lower, for example about 1:2 to less than about 1:1.

SUMMARY OF THE INVENTION

The invention provides a composition comprising (i) about 0.05 to about 0.5% by weight retinol; (ii) a polar emollient selected from the group consisting of propylene glycol stearyl ether, dicaprylyl carbonate, propylene glycol isostearate and combinations thereof; and (iii) isohexadecane, wherein the weight ratio of polar emollient to isohexadecane is 1:1 or lower and the composition is anhydrous.

The invention further provides use of the composition for reducing the signs of skin aging.

The invention also provides use of the composition for reducing the appearance of stretch marks or cellulite.

The invention also provides use of the composition for treating acne or rosacea.

The invention further provides use of the composition for treating uneven skin.

DETAILED DESCRIPTION OF THE INVENTION

Unless defined otherwise, all technical and scientific terms used herein have the same meaning as commonly understood by one of ordinary skill in the art to which the invention belongs. All publications, patent applications, patents, and other references mentioned herein are incorporated by reference.

As used herein, "topical application" or "topically applying" means directly laying on or spreading on outer skin, the scalp, or hair, e.g., by use of the hands or an applicator such as a wipe, roller, or spray.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, "cosmetically effective amount" means an amount of a physiologically active compound or composition sufficient for treating one or more signs of skin aging, but low enough to avoid serious side effects. The cosmetically effective amount of the compound or composition will vary with the particular condition being treated, the age and physical condition of the end user, the severity of the condition being treated/prevented, the duration of the treatment, the nature of other treatments, the specific compound or product/composition employed, the particular cosmetically-acceptable carrier utilized, and like factors.

As used herein, "cosmetically acceptable" means that the ingredients the term describes are suitable for use in contact with tissues (e.g., the skin or hair) without undue toxicity, incompatibility, instability, irritation, allergic response, or the like.

As used herein, a "cosmetically acceptable active agent" is a compound (synthetic or natural) that has a cosmetic or therapeutic effect on the skin or hair.

As used herein, "treating" refers to mitigating, reducing, preventing, improving, or eliminating the presence or signs of a condition or disorder.

The present invention is suitable for treating signs of skin aging. As used herein, "signs of skin aging" includes the presence of lines and wrinkles, loss of elasticity, uneven skin, and blotchiness. In a particularly preferred embodiment, the sign of aging is the presence of lines and wrinkles and/or loss of elasticity.

As used herein, "wrinkle" includes fine lines, fine wrinkles, or coarse wrinkles. Examples of wrinkles include, but are not limited to, fine lines around the eyes (e.g., "crow's feet"), forehead and cheek wrinkles, frown-lines, and laugh-lines around the mouth.

As used herein, "loss of elasticity" includes loss of elasticity or structural integrity of the skin or tissue, including but not limited to sagging, lax and loose tissue. The loss of elasticity or tissue structure integrity may be a result of a number of factors, including but not limited to disease, aging, hormonal changes, mechanical trauma, environmental damage, or the result of an application of products, such as a cosmetics or pharmaceuticals, to the tissue.

As used herein, "uneven skin" means a condition of the skin associated with diffuse or mottled pigmentation, which may be classified as hyperpigmentation, such as post-inflammatory hyperpigmentation.

As used herein, "blotchiness" means a condition of the skin associated with redness or erythema. As used herein, "stretch mark" means pink, reddish or purplish indented streaks that often appear on the abdomen, breasts, upper arms, buttocks and thighs.

As used herein, "cellulite" means pockets of fat, which are trapped and cause dimpling in the skin. The dimpling is irregular and patchy and has been identified with orange peel and cheese skin.

The invention is also suitable for treating acne. As used herein, "acne" refers to disorders resulting from the actions of hormones and other substances on the sebaceous glands and hair follicles, typically leading to clogged pores and the formation of inflammatory or non-inflammatory lesions on the skin. Specifically, it relates to blemishes, lesions, or pimples, pre-emergent pimples, blackheads, and/or whiteheads. As used herein, a "pre-emergent pimple" is an inflamed follicle that are not visually apparent on the surface of the skin with the naked eye (e.g., as a lesion).

The invention is also suitable for treating rosacea. As used herein, "rosacea" means skin with persistent erythema with or without papules, pustules, or nodules.

Unless otherwise indicated, a percentage or concentration refers to a percentage or concentration by weight (i.e., % (W/W). Unless stated otherwise, all ranges are inclusive of the endpoints, e.g., "from 4 to 9" includes the endpoints 4 and 9.

Where applicable, chemicals are specified according to International Nomenclature of Cosmetic Ingredient (INCI) names. Additional information, including suppliers and trade names, can be found under the appropriate INCI monograph in the *International Cosmetic Ingredient Dictionary and Handbook*, 16$^{th}$ Edition published by the Personal Care Products Council, Washington D.C., or via the Personal Care Products Council's On-Line INFOBASE, http://online.personalcarecouncil.org/jsp/Home.jsp.

Retinol

The composition comprises retinol. Retinol has the formula:

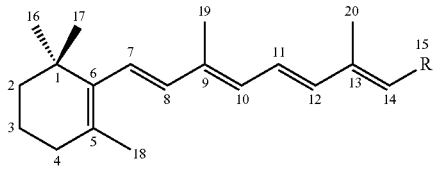

wherein R is CH$_2$OH.

In other embodiments, other retinoids including retinal, retinoic acid, retinyl acetate, retinyl palmitate, amine derivatives, and the like, may be used instead of or in addition to retinol.

The composition may contain a cosmetically effective amount of retinol. The composition preferably contains from about 0.001% to about 2% of retinol, more preferably from about 0.01% to about 1% of retinol.

In one embodiment, the composition comprises about 0.05 to about 0.5 percent by weight retinol.

Retinol may be obtained for example from BASF.

Polar Emollient

The composition also contains a polar emollient selected from the group consisting of propylene glycol stearyl ether, dicaprylyl carbonate, propylene glycol isostearate and combinations thereof.

In one embodiment, the polar emollient is a combination of propylene glycol stearyl ether and dicaprylyl carbonate.

Propylene glycol stearyl may be obtained commercially from either Croda or Evonik.

Dicaprylyl carbonate may be obtained commercially from BASF.

In one embodiment, the composition contains about 1 to about 50 weight percent polar emollient, preferably about 15 to about 25 weight percent polar emollient.

Isohexadecane

The composition also contains isohexadecane.

In one embodiment, the composition contains about 19 to about 70 weight percent isohexadecane, preferably about 30 to about 60 weight percent isohexadecane.

Isohexadecane may be obtained commercially, for example, from Croda or Presperse.

Weight Ratio of Polar Emollient to Isohexadecane

Regardless of the amount of retinol in the composition, the weight ratio of polar emollient to isohexadecane is 1:1 or lower, for example about 1:2 to less than about 1:1.

In one embodiment, the weight ratio of polar emollient to isohexadecane is about 1:2 to about 1:1.

In one embodiment, the weight ratio of polar emollient to isohexadecane is about 1:2.

In a particular embodiment, the polar emollient is a combination of propylene glycol stearyl ether and dicaprylyl carbonate and the weight ratio of polar emollient to isohexadecane is about 1:2.

Oil Composition

The composition is an oil composition. That is, it is anhydrous.

As used herein, an "oil" or "anhydrous" composition means the composition includes less than about 0.25% by weight water. In a preferred embodiment, the composition comprises less than about 0.1% of water. In yet a further preferred embodiment, the composition is completely free of water. These maximum levels of water may, in certain embodiments refer only to "free" water, i.e., water that is not chemically bound to another compound (e.g., in a crystal as water of hydration).

The composition may therefore contain any hydrophobic components typically used in anhydrous cosmetic compositions. A wide variety of hydrophobic components may be used at their art-established levels. The hydrophobic component may be derived from animals, plants, or petroleum and may be natural or synthetic.

Nonlimiting examples of suitable hydrophobic components include the following.

(1) Mineral oil, which is also known as petrolatum liquid, is a mixture of liquid hydrocarbons obtained from petroleum.

(2) Petrolatum, which is also known as petroleum jelly, is a colloidal system of non-straight-chain solid hydrocarbons and high-boiling liquid hydrocarbons, in which most of the liquid hydrocarbons are held inside the micelles.

(3) Straight and branched chain hydrocarbons having from about 7 to about 40 carbon atoms. Nonlimiting examples include dodecane, isododecane, squalane, cholesterol, hydrogenated polyisobutylene, docosane (i.e. a C22 hydrocarbon), and hexadecane. Also useful are the C7-C40 isoparaffins, which are C7-C40 branched hydrocarbons.

(4) C1-C30 alcohol esters of C1-C30 carboxylic acids and of C2-C30 dicarboxylic acids, including straight and branched chain materials as well as aromatic derivatives (mono- and poly-carboxylic acids include straight chain, branched chain and aryl carboxylic acids). Nonlimiting examples include diisopropyl sebacate, diisopropyl adipate, isopropyl myristate, isopropyl palmitate, methyl palmitate, myristyl propionate, 2-ethylhexyl palmitate, isodecyl neopentanoate, di-2-ethylhexyl maleate, cetyl palmitate, myristyl myristate, stearyl stearate, isopropyl stearate, methyl stearate, cetyl stearate, behenyl behenrate, dioctyl maleate, dioctyl sebacate, diisopropyl adipate, cetyl octanoate, diisopropyl dilinoleate.

(5) mono-, di- and tri-glycerides of C1-C30 carboxylic acids, e.g., caprilic/capric triglyceride, PEG-6 caprylic/capric triglyceride, PEG-8 caprylic/capric triglyceride.

(6) alkylene glycol esters of C1-C30 carboxylic acids, e.g., ethylene glycol mono- and di-esters, and propylene glycol mono- and di-esters of C1-C30 carboxylic acids e.g., ethylene glycol distearate.

(7) propoxylated and ethoxylated derivatives of the foregoing materials.

(8) C1-C30 mono- and poly-esters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose heptaoleate, sucrose octaoleate, and mixtures thereof.

(9) Organopolysiloxane oils. The organopolysiloxane oil may be volatile, non-volatile, or a mixture of volatile and non-volatile silicones. Nonlimiting examples of suitable organopolysiloxane oils include polyalkylsiloxanes, cyclic polyalkylsiloxanes, and polyalkylarylsiloxanes.

Polyalkylsiloxanes include polyalkylsiloxanes with viscosities of from about 0.5 to about 1,000,000 centistokes at 25° C. Commercially available polyalkylsiloxanes include the polydimethylsiloxanes, which are also known as dimethicones, examples of which include the VICASIL series sold by General Electric Company and the DOW CORNING 200 series sold by Dow Corning Corporation. Specific examples of suitable polydimethylsiloxanes include DOW CORNING 200 fluid, DOW CORNING 225, cetyl dimethicone, lauryl dimethicone, and cyclic polyalkylsiloxanes such as DOW CORNING 244, DOW CORNING 344, DOW CORNING 245, DOW CORNING 345 DOW CORNING 593 fluid, DOW CORNING 1401, 1402, and 1403 fluids.

(10) Vegetable oils and hydrogenated vegetable oils. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

(11) Animal fats and oils, e.g., lanolin and derivatives thereof, cod liver oil.

(12) Also useful are C4-C20 alkyl ethers of polypropylene glycols, C1-C20 carboxylic acid esters of polypropylene glycols, and di-C8-C30 alkyl ethers. Nonlimiting examples of these materials include PPG-14 butyl ether, dioctyl ether, dodecyl octyl ether, and mixtures thereof.

The composition may comprise a variety of other materials known in the art including emulsifiers, pearlescent or opacifying agents, thickeners, emollients, conditioners, humectants, chelating agents, exfoliants, and additives that enhance the appearance, feel, or fragrance of the composition, such as colorants, fragrances, The composition may further comprise other cosmetically acceptable active agents provided they are suitable for anhydrous compositions, for example anti-acne agents, shine control agents, anti-microbial agents, anti-inflammatory agents, anti-mycotic agents, anti-parasite agents, external analgesics, sunscreens, photoprotectors, antioxidants, keratolytic agents, surfactants, moisturizers, nutrients, vitamins, energy enhancers, anti-perspiration agents, astringents, deodorants, firming agents, anti-callous agents, and agents for hair and/or skin conditioning.

The amount of other cosmetically active agent may range from about 0.001% to about 20% by weight of the composition, e.g., about 0.005% to about 10% by weight of the composition, such as about 0.01% to about 5% by weight of the composition.

The composition may be in the form of an ointment that contains organic and/or silicone solvents, oils, lipids and waxes. An ointment may contain a simple base of animal or vegetable oils or semi-solid hydrocarbons. An ointment may contain from about 2% to about 10% of an emollient(s) plus from about 0.1% to about 2% of a thickening agent(s). Examples of thickening agents include, but are not limited to, those set forth in the ICI Handbook pp. 2979-84.

The following examples further illustrate the claimed invention.

Example 1

A series of oil formulations containing different amounts of retinol, PPG15 stearyl ether, dicaprylyl carbonate and isohexadecane were made and tested for retinol activity and irritation.

The formulations were anhydrous and contained 0.1%, 0.3%, or 0.5% by weight of retinol, which was used in the form of a 50/50 wt % mixture with polysorbate 20. The retinol was dissolved in an oil formulation containing PPG15 stearyl ether, dicaprylyl carbonate and isohexadecane, and the other ingredients shown in Table 2. The amount of PPG15 stearyl ether in each formulation was 18% by weight, while the amount of dicaprylyl carbonate was varied.

TABLE 2

| INCI | Formula A % w/w | Formula B % w/w | Formula C % w/w | Formula D % w/w | Formula E % w/w | Formula F % w/w | Formula G % w/w | Formula H % w/w | Formula I % w/w |
|---|---|---|---|---|---|---|---|---|---|
| Dicaprylyl Carbonate | 1.47 | 8.27 | 21.47 | 40.27 | 7.83 | 22.83 | 33.83 | 8.41 | 33.41 |
| PPG-15 Stearyl Ether | 18.00 | 18.00 | 18.00 | 18.00 | 18.00 | 18.00 | 18.00 | 18.00 | 18.00 |

TABLE 2-continued

| INCI | Formula A % w/w | Formula B % w/w | Formula C % w/w | Formula D % w/w | Formula E % w/w | Formula F % w/w | Formula G % w/w | Formula H % w/w | Formula I % w/w |
|---|---|---|---|---|---|---|---|---|---|
| Isohexadecane | 62.00 | 51.00 | 38.00 | 19.00 | 51.00 | 40.00 | 25.00 | 50.00 | 25.00 |
| Pentaerythrityl Tetraethylhexanoate | 18.00 | 18.00 | 18.00 | 18.00 | 18.00 | 18.00 | 18.00 | 18.00 | 18.00 |
| BHT | 0.10 | 0.10 | 0.10 | 0.10 | 0.10 | 0.10 | 0.10 | 0.10 | 0.10 |
| Triethyl Citrate | N/A | 4.00 | 4.00 | 4.00 | 4.00 | N/A | 4.00 | 4.00 | 4.00 |
| Tocopheryl Acetate | 0.20 | 0.20 | 0.20 | 0.20 | 0.20 | 0.20 | 0.20 | 0.20 | 0.20 |
| Bisabolol | N/A | 0.20 | N/A | 0.20 | 0.20 | 0.20 | 0.20 | 0.20 | 0.20 |
| 50% Polysorbate 20; 50% Retinol | 0.23 | 0.23 | 0.23 | 0.23 | 0.67 | 0.67 | 0.67 | 1.09 | 1.09 |
| Total | 100.00 | 100.00 | 100.00 | 100.00 | 100.00 | 100.00 | 100.00 | 100.00 | 100.00 |

Table 3 shows the amounts of retinol, polar emollients, isohexadecane, and weight ratio of polar emollients to isohexadecane in each of the formulations.

TABLE 3

| | Retinol level (wt %) | Polar Emollients (Dicaprylyl Carbonate and PPG15 Stearyl Ether) (wt %) | Isohexadecane (wt %) | Weight Ratio of Polar Emollients to Isohexadecane |
|---|---|---|---|---|
| Formula A | 0.1 | 19.5 | 62 | 1:3 |
| Formula B | 0.1 | 26.3 | 51 | 1:2 |
| Formula C | 0.1 | 39.5 | 38 | 1:1 |
| Formula D | 0.1 | 58.3 | 19 | 3:1 |
| Formula E | 0.3 | 25.8 | 51 | 1:2 |
| Formula F | 0.3 | 40.8 | 40 | 1:1 |
| Formula G | 0.3 | 51.8 | 25 | 2:1 |
| Formula H | 0.5 | 26.4 | 50 | 1:2 |
| Formula I | 0.5 | 51.4 | 25 | 2:1 |

The retinol activity and retinol irritation effect of each formulation were measured in vitro by assessing the level of Cellular Retinoic Acid Binding Protein 2 (CRABP2) gene expression and interleukin 8 (IL8) gene expression, respectively. The gene expression tests were performed on human skin explants as follows.

Formulations A-I were applied topically to the explants and incubated for 48 hours. Untreated tissue was used as the baseline control. For each formulation changes in CRABP2 and IL8 gene expression were measured by quantitative polymerase chain reaction (qPCR) assays. After the 48-hour incubation, total RNAs were isolated from each skin explant tissues using an Qiagen RNeasy Mini kit for fibrous tissues (Valencia, Calif., USA) following the manufacturer's instructions. RNA concentration was assessed using a Nanodrop 2000 spectrophotometer (Thermo Fisher Scientific, Hudson, N.H., USA).

Reverse transcription was performed using a High Capacity cDNA kit (Life Technologies Corporation, Grand Island, N.Y., USA).

qPCR was used to screen for the expression of CRABP2, IL8 and the human TATA-binding protein (TBP) housekeeping gene. TaqMan® gene expression assays for CRABP2, IL8, and TBP, and TaqMan® gene expression master mix were purchased from Life Technologies Corporation (Grand Island, N.Y., USA).

qPCR was performed using an ABI 7500 Fast Real-Time PCR system (Life Technologies Corporation, Grand Island, N.Y., USA). Each reaction was carried out by ribonucleic acid (RNA) from individual tissue explant, and normalized to the TBP. The fold changes were calculated in comparison with the untreated control.

The results were first normalized by the corresponding untreated control results. The results normalized for control were then further normalized by the results obtained by treating the explants with NEUTROGENA® Rapid Wrinkle Repair® as a positive control. The ingredients in NEUTROGENA® Rapid Wrinkle Repair® are shown in Table 4.

TABLE 4

Water
pentaerythrityl tetraethylhexanoate
dimethicone
glycerin
PPG-15 stearyl ether
stearyl alcohol
cetearyl alcohol
butylene glycol
trisiloxane
ceteareth-20
isohexadecane
dimethicone crosspolymer
retinol
hydrolyzed myrtus communis leaf extract
BHT
ascorbic acid
caprylyl glycol
sodium hyaluronate
polyethylene
ammonium acryloyldimethyltaurate/VP copolymer
C13-14 isoparaffin
polyacrylamide
PTFE
polysorbate 20
laureth-7
sodium hydroxide
disodium EDTA
chlorphenesin
phenoxyethanol
fragrance The gene expression results are shown in Table 5, which includes the ratio of the normalized CRABP2 value to normalized IL8 value.

TABLE 5

| Formula | Emollient Ratio | Normalized CRABP2 | Normalized IL-8 | Normalized CRABP2/IL8 |
|---|---|---|---|---|
| A | 1:3 | 0.913 | 1.909 | 0.478 |
| B | 1:2 | 0.792 | 0.429 | 1.845 |
| C | 1:1 | 0.616 | 0.651 | 0.946 |
| D | 3:1 | 0.267 | 0.757 | 0.352 |
| E | 1:2 | 1.351 | 0.902 | 1.497 |
| F | 1:1 | 1.109 | 1.050 | 1.057 |
| G | 2:1 | 0.604 | 0.714 | 0.846 |
| H | 1:2 | 1.460 | 0.592 | 2.467 |
| I | 2:1 | 1.013 | 0.957 | 1.059 |

The results in Table 5 show that regardless of the dose of retinol, oil formulas having an emollient ratio of 1:2 (i.e. Formulas B, E and H) displayed the highest Normalized CRABP2/IL8 ratios, indicating the best of activity-to-irritation ratio.

In addition, at a retinol dose of 0.3 weight %, the emollient ratio of 1:1 (Formula F) displayed the second highest activity-to-irritation ratio, whereas a retinol dose of 0.3 weight % coupled with an emollient ratio of 2:1 (Formula G) showed a lower activity.

Example 2

A composition according to the invention was prepared having the ingredients shown in Table 6.

TABLE 6

| INCI | % w/w |
| --- | --- |
| Dicaprylyl Carbonate | 7.83 |
| PPG-15 Stearyl Ether | 18.00 |
| Isohexadecane | 51.00 |
| Pentaerythrityl Tetraethylhexanoate | 18.00 |
| BHT | 0.10 |
| Triethyl Citrate | 4.00 |
| Tocopheryl Acetate | 0.20 |
| Bisabolol | 0.20 |
| Polysorbate 20; Retinol | 0.67 |

The composition was prepared as follows. Dicaprylyl carbonate was added to a mixing vessel and mixing began. PPG-15 stearyl ether, isohexadecane, pentaerythrityl tetraethylhexanoate, BHT, tocopheryl acetate, triethyl citrate, bisabolol, and retinol were added to the mixing vessel one at a time allowing for proper mixing, and mixed until homogeneous.

The invention claimed is:

1. A composition comprising (i) about 0.05 to about 0.5% by weight retinol; (ii) a polar emollient selected from the group consisting of propylene glycol stearyl ether, dicaprylyl carbonate, propylene glycol isostearate and combinations thereof; and (iii) isohexadecane, wherein the weight ratio of polar emollient to isohexadecane is 1:1 or lower and the composition is anhydrous.

2. The composition of claim 1, wherein the weight ratio of polar emollient to isohexadecane is about 1:2.

3. The composition of claim 1 wherein the polar emollient is a combination of propylene glycol stearyl ether and dicaprylyl carbonate.

4. A method of treating signs of skin aging comprising topically applying to skin in need of treatment for signs of skin aging the composition of claim 1.

5. A method of treating stretch marks or cellulite comprising topically applying to skin in need of treatment for stretch marks or cellulite the composition of claim 1.

6. A method of treating acne or rosacea comprising topically applying to skin in need of treatment for acne or rosacea the composition of claim 1.

* * * * *